United States Patent [19]

Hooper et al.

[11] 4,292,192
[45] Sep. 29, 1981

[54] PERSONAL WASHING DETERGENT BARS WITH AN EFFECTIVE AMOUNT OF A CITRIC ACID ESTER

[75] Inventors: David C. Hooper, Ashford; George A. Johnson; Donald Peter, both of Wirral, all of England

[73] Assignee: Lever Brothers Company, New York, N.Y.

[21] Appl. No.: 159,320

[22] Filed: Jun. 13, 1980

Related U.S. Application Data

[63] Continuation of Ser. No. 877,534, Feb. 13, 1978, abandoned, which is a continuation-in-part of Ser. No. 826,079, Aug. 19, 1977, abandoned.

[30] Foreign Application Priority Data

Aug. 20, 1976 [GB] United Kingdom ............... 34788/76

[51] Int. Cl.³ ...................... C11D 17/00; C11D 9/26; A61K 7/32
[52] U.S. Cl. .................................... 252/132; 252/106; 252/107; 252/134; 252/174; 252/174.19; 252/DIG. 16
[58] Field of Search ......... 252/134, 174, 132, DIG. 5, 252/DIG. 16, 106, 107, 174.19, 174.11; 424/65, 47

[56] References Cited

U.S. PATENT DOCUMENTS

| | | | |
|---|---|---|---|
| 2,948,684 | 8/1960 | Thiele | 424/65 X |
| 3,792,158 | 2/1974 | Fein et al. | 424/65 |
| 3,833,721 | 9/1974 | Saute et al. | 424/47 |
| 3,912,667 | 10/1975 | Spitzer et al. | 260/2.5 E |
| 4,010,253 | 3/1977 | Reese et al. | 424/47 |

FOREIGN PATENT DOCUMENTS 7604601 8/1977 Brazil .
2208248 9/1973 Fed. Rep. of Germany .

*Primary Examiner*—P. E. Willis, Jr.
*Attorney, Agent, or Firm*—James J. Farrell; Melvin H. Kurtz; Irving N. Feit

[57] ABSTRACT

Detergent bars for personal washing are given a deodorant property by including an ester of citric acid. The ester may be an acetyl derivative. The amount of ester used will be in the range of from about 0.3% to about 3%. Examples of the esters are triethyl citrate and acetyl tributyl citrate.

6 Claims, No Drawings

PERSONAL WASHING DETERGENT BARS WITH AN EFFECTIVE AMOUNT OF A CITRIC ACID ESTER

This application is a continuation application of application Ser. No. 877,534 filed Feb. 13, 1978 and now abandoned which in turn was a continuation-in-part application of application Ser. No. 826,079 filed Aug. 19, 1977 and now abandoned.

This invention relates to detergent bars intended for use in personal washing.

A useful commercial property for detergent bars of this class is the ability to provide a deodorancy effect on the skin. The present invention describes detergent bars capable of providing a deodorancy effect and containing from about 0.3% to about 3% by weight of an ester of citric acid, or an acetyl derivative thereof, with the formula

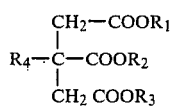

wherein $R_1$, $R_2$ and $R_3$ are each hydrogen or an alkyl group containing from 1 to 4 carbon atoms, provided at least one of $R_1$, $R_2$ and $R_3$ is an alkyl group and $R_4$ is hydroxyl or a $CH_3COO-$ group. Preferably the bar contains from about 0.5% and preferably up to about 1% by weight of the ester. The optimum level is about 0.75%. The preferred members of the $R_1$, $R_2$, $R_3$ alkyl radicals are ethyl and butyl. The ester is preferably a triester. The remainder of the bar will comprise detergent active material and other components, for example perfumes, pigments, water content, opacifiers, germicides, preservatives, inorganic salts, plasticisers and pH controlling additives.

The detergent bars of the invention will contain detergent active materials from the classes of soaps, anionic actives, cationic actives, nonionic actives and zwitterionic actives. Examples of detergent actives usable to form the detergent bars of the invention will be found in "Surface Active Agents" by Schwartz & Perry (Interscience 1949) and "Surface Active Agents" Vol 2, by Schwartz, Perry & Berch (Interscience 1958). Specific examples of detergent active materials are listed in UK patent specification No. 1460442. (German specification No. 2401752) The term "soap" is used to define water soluble salts of long chain aliphatic acids containing from 8 to 24 carbon atoms in the alkyl chain, and these are preferred actives. These salts may be of alkali metals or ammonium and the acids may be derived from natural sources or through synthetic routes.

The citrate ester is preferably incorporated at the mixing stage for additional ingredients. At this stage perfume and pigments will be added. The detergent material will then be subjected to the steps of milling, plodding, extrusion and stamping to form bars.

The benefit of skin deodorancy is achieved from the detergent bars of the present invention even though the materials providing the deodorancy benefit are contacted with the skin in the presence of a solution of a detergent active material and the skin is subsequently subjected to rinsing after washing. The citric acid derivatives providing the deodorancy benefit retain their ability during storage in a detergent bar in the presence of detergent active materials and a water content. The water content of soap bars is usually in the range 8% to 10%. Bars containing detergent actives other than soap may have a water content as low as about 5% or as high as about 15%.

Examples of the citric acid derivatives included within the formula are triethyl citrate, acetyltributyl citrate and acetyl triethylcitrate.

Examples of detergent bars according to the invention will now be given.

Soap bars containing 80 parts tallow soap, 20 parts coconut soap of which 5 parts are free fatty acids (expressed as coconut oil fatty acids) were prepared containing the citric acid derivative in the amount specified in Table I. Control soap bars were also prepared.

A panel of 40 subjects was used to test the deodorancy effect achieved with the test soap bars on the axillary areas. Control bars were used to wash one armpit and test bars the other armpit of each subject. Olfactory assessment of the odour level in each armpit was performed five hours after washing on a scale 0 to 5, with the latter limit being the strongest odour. The averages of the scale assessment are given in Table I and are the means of the assessments taken on four consecutive days.

TABLE I

| Derivative | Level | Test Bar | Control Bar | Difference |
|---|---|---|---|---|
| Acetyl tributyl citrate | 1% | 2.71 | 2.99 | 0.28 |
| Acetyl triethyl citrate | 1% | 2.60 | 2.80 | 0.20 |
| Triethyl citrate | 0.5% | 3.05 | 3.29 | 0.24 |
| Triethyl citrate | 1% | 2.68 | 3.13 | 0.45 |

Difference for significance at 95% confidence = 0.20.

The deodorant effect provided by acetyl tributyl citrate (ATBC) was studied using different concentrations, assessment periods and formulations. The test procedure was that described above and the results are given in Table II.

TABLE II

| Level of ATBC (% weight) | Assessment time after washing | Test Bar | Control Bar | Difference |
|---|---|---|---|---|
| 0.25* | 5 hours | 3.28 | 3.13 | −0.15 |
| 0.5 | 5 hours | 2.73 | 2.93 | 0.20 |
| 0.75 | 5 hours | 2.53 | 2.93 | 0.40 |
| 1.00 | 24 hours | 2.67 | 2.92 | 0.25 |
| 0.75 | 24 hours | 3.16 | 3.36 | 0.20 |
| 0.75** | 5 hours | 2.62 | 3.07 | 0.45 |

*The difference between the bars demonstrates the level is not sufficient to provide a significant deodorant effect.
**The detergent base used was that of the previous tests but included 1.5% perfume, thus a significant deodorant effect was achieved in the presence of perfume.

What is claimed is:
1. A detergent bar comprising:
(i) from about 0.3% to about 3% by weight of an optionally acetylated ester of citric acid of formula

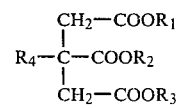

wherein $R_1$ $R_2$ and $R_3$ are hydrogen or an alkyl group containing from 1 to 4 carbon atoms, provided at least one of $R_1$ $R_2$ and $R_3$ is an alkyl group, and $R_4$ is a hydroxyl or a $CH_3COO-$ group;
(ii) a water content of from about 5% and;
(iii) up to about 94.7% of detergent active material and other components of detergent bars.

2. A detergent bar according to claim 1 wherein the ester is a tri-ester.

3. A detergent bar according to claim 1 or 2 wherein $R_1 R_2$ and $R_3$ are each hydrogen, ethyl or butyl.

4. A detergent bar according to claim 1 wherein the citric acid ester is present in an amount from about 0.5%.

5. A detergent bar according to claim 1 wherein the citric acid ester is present in an amount up to about 1.0%.

6. A detergent bar according to claim 1 wherein the detergent active material includes water soluble salts of long chain ($C_8$ to $C_{24}$) aliphatic acids.

* * * * *